(12) United States Patent  
Komoda (10) Patent No.: US 10,441,217 B2  
(45) Date of Patent: Oct. 15, 2019

(54) EYEWEAR SET AND SIGNAL PROCESSING UNIT

(71) Applicant: JINS HOLDINGS INC., Gunma (JP)

(72) Inventor: Taiki Komoda, Tokyo (JP)

(73) Assignee: JINS HOLDINGS Inc., Gunma (JP)

( * ) Notice: Subject to any disclaimer, the term of this patent is extended or adjusted under 35 U.S.C. 154(b) by 0 days.

(21) Appl. No.: 16/157,095

(22) Filed: Oct. 11, 2018

(65) Prior Publication Data

US 2019/0239770 A1 Aug. 8, 2019

(51) Int. Cl.
| | |
|---|---|
| *A61B 5/00* | (2006.01) |
| *A61B 5/0496* | (2006.01) |
| *G02C 11/00* | (2006.01) |
| *G02C 5/12* | (2006.01) |
| *G02C 5/02* | (2006.01) |

(52) U.S. Cl.
CPC .......... *A61B 5/6803* (2013.01); *A61B 5/0496* (2013.01); *A61B 5/6819* (2013.01); *G02C 5/02* (2013.01); *G02C 5/12* (2013.01); *G02C 11/10* (2013.01)

(58) Field of Classification Search
CPC ....... A61B 3/10; A61B 5/0496; A61B 5/6803; A61B 5/6814; A61B 5/6821; G02C 11/00; G02C 11/10
See application file for complete search history.

(56) References Cited

U.S. PATENT DOCUMENTS

| | | | | |
|---|---|---|---|---|
| 8,172,419 | B1 * | 5/2012 | Gasparre | F21L 4/005 |
| | | | | 362/103 |
| 2002/0188216 | A1 * | 12/2002 | Kayyali | A61B 5/04085 |
| | | | | 600/544 |
| 2013/0324881 | A1 | 12/2013 | Kanoh | |
| 2014/0228652 | A1 * | 8/2014 | Terada | A61B 5/0478 |
| | | | | 600/301 |

(Continued)

FOREIGN PATENT DOCUMENTS

| | | | | |
|---|---|---|---|---|
| JP | 2013244370 A | * | 12/2013 | ............... A61B 3/10 |
| JP | 2017157139 A | * | 9/2017 | ............... A61B 3/10 |
| WO | WO-2016194848 A1 | * | 12/2016 | ............... A61B 3/10 |

OTHER PUBLICATIONS

Office Action issued for counterpart Japanese Application No. 2018-020185, issued by the Japan Patent Office dated Feb. 12, 2019 (drafted on Feb. 7, 2019).

*Primary Examiner* — Eun Hwa Kim (57) ABSTRACT

An eyewear set is provided, including: an eyewear; and a signal processing unit that is attachable to and detachable from a bridge of the eyewear, where the signal processing unit includes: an enclosure; a first electrode and a second electrode that are provided outside the enclosure and detect a biomedical signal of a wearer who is wearing the eyewear; a signal processing portion that is arranged inside the enclosure and processes the biomedical signal; a transmitting portion that is arranged inside the enclosure and transmits a processing result according to the signal processing portion to an external device; a power supply portion that is (Continued)

arranged inside the enclosure and supplies electrical power to the signal processing portion and the transmitting portion; and a mounting portion that attachably and detachably mounts the enclosure on the bridge.

11 Claims, 5 Drawing Sheets

(56) References Cited

U.S. PATENT DOCUMENTS

| | | | |
|---|---|---|---|
| 2015/0229813 A1* | 8/2015 | Isaac-Lowry | H04N 5/2252 |
| | | | 348/376 |
| 2016/0132107 A1* | 5/2016 | Kanishima | G06F 3/015 |
| | | | 345/633 |
| 2017/0027470 A1 | 2/2017 | Inoue | |
| 2018/0004008 A1* | 1/2018 | Froissard | G02C 1/02 |
| 2018/0049664 A1* | 2/2018 | Miyazaki | A61B 3/10 |
| 2018/0064371 A1* | 3/2018 | Yamada | A61B 5/1116 |
| 2018/0160973 A1 | 6/2018 | Inoue | |

* cited by examiner

EYEWEAR SET AND SIGNAL PROCESSING UNIT

The contents of the following Japanese patent application(s) are incorporated herein by reference:
NO. 2018-020185 filed on Feb. 7, 2018

BACKGROUND

1. Technical Field

The present invention relates to an eyewear set and a signal processing unit.

2. Related Art

An eyewear to detect a biomedical signal of a wearer who is wearing the eyewear and to perform a processing which is based on the detected biomedical signal has been known (for example, refer to Patent Document 1).

PRIOR ART LITERATURE

Patent Document

[Patent Document 1] Japanese Patent Application Publication No. 2013-244370

In a case where an electronic device is to be mounted on an eyewear, it is desirable to achieve eyewear strength and reliability against bending and the like, and naturalness of appearance of the eyewear.

SUMMARY

According to a first aspect of the present invention, an eyewear set is provided. The eyewear set may include an eyewear, and a signal processing unit that is attachable to and detachable from a bridge of the eyewear. The signal processing unit may include an enclosure. The signal processing unit may include a first electrode and a second electrode that are provided outside the enclosure and detect a biomedical signal of a wearer who is wearing the eyewear. The signal processing unit may include a signal processing portion that is arranged inside the enclosure and processes the biomedical signal. The signal processing unit may include a transmitting portion that is arranged inside the enclosure and transmits a processing result according to the signal processing portion to an external device. The signal processing unit may include a power supply portion that is arranged inside the enclosure and supplies electrical power to the signal processing portion and the transmitting portion. The signal processing unit may include a mounting portion that attachably and detachably mounts the enclosure on the bridge.

The above-described signal processing unit may include a pair of abutting portions positioned to abut on a nose of the above-described wearer, and the above-described first electrode and the above-described second electrode may be installed on a surface of each of the above-described pair of abutting portions and may detect an ocular potential of the above-described wearer. The above-described signal processing unit may include a third electrode positioned to abut on a glabella of the above-described wearer. The above-described first electrode may be installed on a lower side than a center of one of the above-described pair of abutting portions, and the above-described second electrode may be provided on an upper side than a center of the other of the above-described pair of abutting portions. The above-described first electrode and the above-described second electrode may be positioned to abut on the glabella of the above-described wearer and detect the ocular potential of the above-described wearer.

The above-described mounting portion may include a hole that communicates with a hole provided in a bridge of the above-described eyewear. The above-described mounting portion may mount the above-described enclosure on the above-described bridge by sandwiching a frame of the above-described eyewear. The above-described eyewear and the above-described signal processing unit may not be electrically connected to each other.

According to a second aspect of the present invention, a signal processing unit is provided. The signal processing unit may include an enclosure. The signal processing unit may include a first electrode and a second electrode that are provided outside the enclosure and detect a biomedical signal. The signal processing unit may include a signal processing portion that is arranged inside the enclosure and processes the biomedical signal. The signal processing unit may include a transmitting portion that is arranged inside the enclosure and transmits a processing result according to the signal processing portion to an external device. The signal processing unit may include a power supply portion that is arranged inside the enclosure and supplies electrical power to the signal processing portion and the transmitting portion. The signal processing unit may include a mounting portion that attachably and detachably mounts the enclosure on the eyewear.

The summary clause does not necessarily describe all necessary features of the embodiments of the present invention. The present invention may also be a sub-combination of the features described above.

DESCRIPTION OF EXEMPLARY EMBODIMENTS

Hereinafter, some embodiments of the present invention will be described. The embodiments do not limit the invention according to the claims, and all the combinations of the features described in the embodiments are not necessarily essential to means provided by aspects of the invention.

Figure 1:
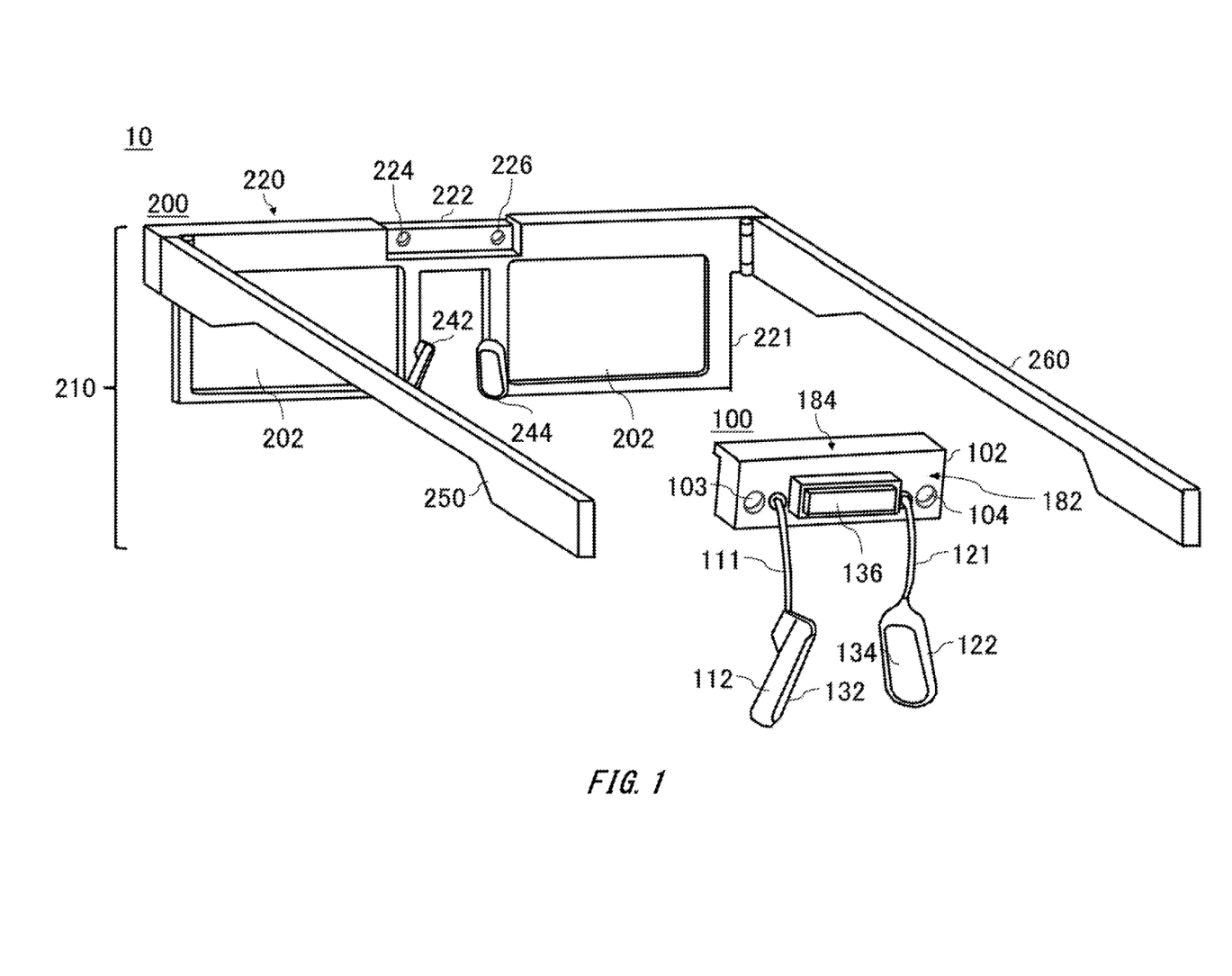
FIG. 1 schematically shows one example of an eyewear set 10.
Figure 2:
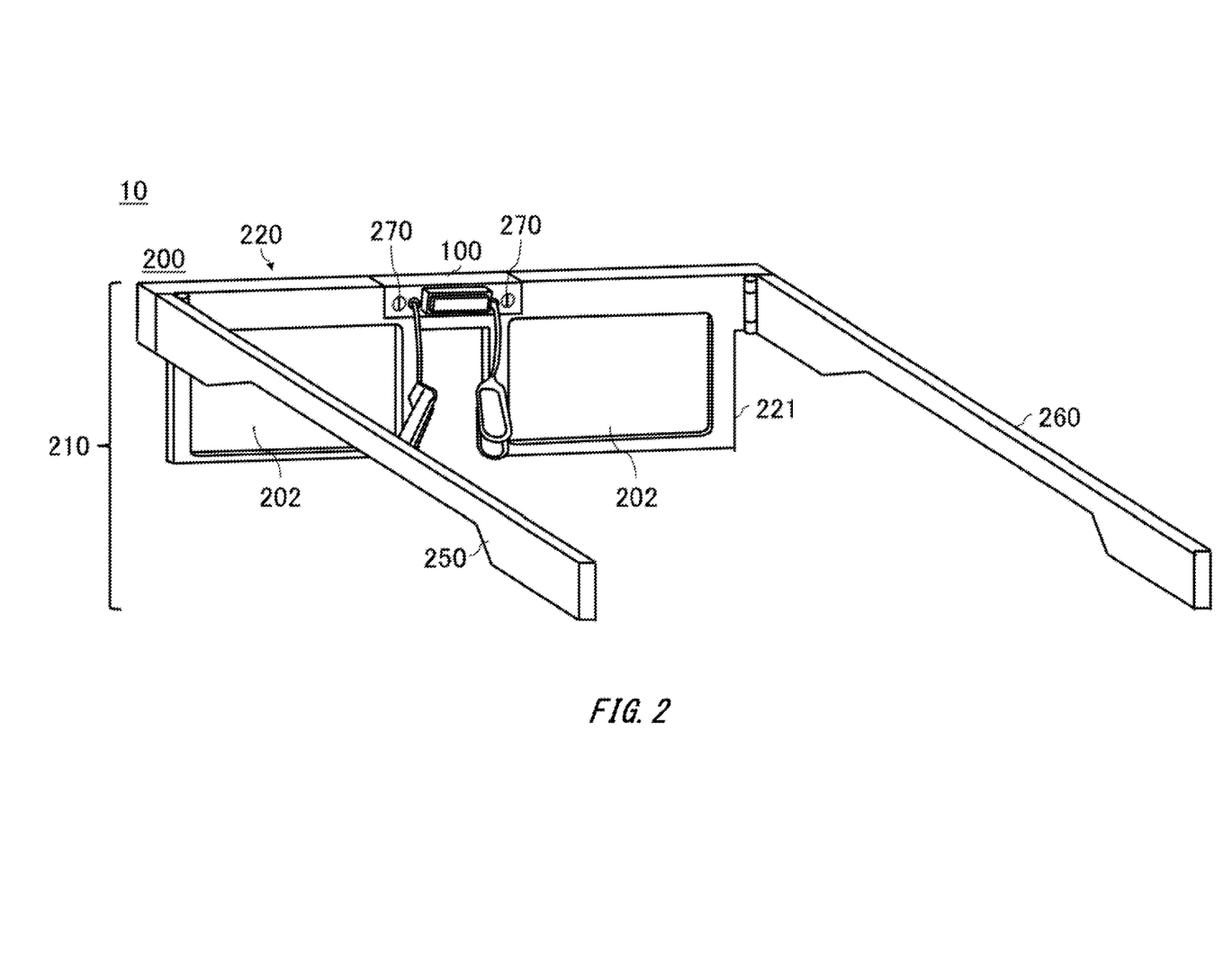
FIG. 2 schematically shows one example of the eyewear set 10.

FIG. 1 and FIG. 2 schematically show one example of an eyewear set 10. The eyewear set 10 includes a pair of glasses 200, and a signal processing unit 100 that is attachable to and detachable from a bridge 222 of the pair of glasses 200. FIG. 1 illustrates a state in which the signal processing unit 100 and the pair of glasses 200 are separated from each other. FIG. 2 illustrates a state in which the signal processing unit 100 is mounted on the pair of glasses 200.

The pair of glasses 200 includes lenses 202 and a frame 210. The pair of glasses 200 may be one example of the eyewear. The frame 210 may be one example of the eyewear.

The frame 210 includes a front portion 220, a temple 250 and a temple 260. The front portion 220 turnably supports the temple 250 and the temple 260. The front portion 220 includes a rim 221, a bridge 222, a nose pad 242 and a nose pad 244. The rim 221 supports the lenses 202. The nose pad 242 and the nose pad 244 are positioned to abut on a nose of a wearer of the pair of glasses 200. The pair of glasses 200 may be utilizable by the wearer even in a state in which the signal processing unit 100 is not mounted.

The bridge 222 according to the present embodiment has a structure that allows the signal processing unit 100 to be mounted thereon. In the example shown in FIG. 1, the bridge 222 has a structure that allows the signal processing unit 100 to be fitted thereinto. Also, the bridge 222 includes a hole 224 and a hole 226 for fixing the signal processing unit 100 by using screws and the like. FIG. 2 shows an example in which the signal processing unit 100 is fixed to the bridge 222 by screws 270.

The signal processing unit 100 includes an enclosure 102, a support portion 111 provided outside the enclosure 102, an abutting portion 112, a support portion 121, an abutting portion 122, an electrode 132, an electrode 134 and an electrode 136. The enclosure 102 includes a hole 103 and a hole 104 that respectively communicate with the hole 224 and the hole 226 provided in the bridge 222. The hole 103 and the hole 104 may be one example of the mounting portion that attachably and detachably mounts the enclosure 102 on the bridge 222.

The abutting portion 112 and the abutting portion 122 may be one example of the pair of abutting portions positioned to abut on the nose of the wearer. The support portion 111 supports the abutting portion 112. The electrode 132 is installed on a surface of the abutting portion 112. The support portion 121 supports the abutting portion 122. The electrode 134 is installed on the surface of the abutting portion 122. If the signal processing unit 100 is mounted on the pair of glasses 200, the abutting portion 112 and the abutting portion 122 may function as the nose pads. If the signal processing unit 100 is not mounted on the pair of glasses 200, the nose pad 242 and the nose pad 244 are positioned to abut on the nose of the wearer. The electrode 136 is installed on a front surface 182 of the enclosure 102 and is positioned to abut on the glabella of the wearer. The electrode 132, the electrode 134 and the electrode 136 detect the biomedical signal of the wearer. The electrode 132, the electrode 134 and the electrode 136 detect the ocular potential of the wearer, for example.

A shape of the enclosure 102 and a shape of the bridge 222 are not limited to the examples shown in FIG. 1 and FIG. 2, and may be any shape. For example, in a case where the enclosure 102 is mounted on the bridge 222, the enclosure 102 and the bridge 222 have any shape so that the enclosure 102 does not protrude from the frame 210. Also, in the case where the enclosure 102 is mounted on the bridge 222, the enclosure 102 and the bridge 222 may also have any shape so that the enclosure 102 protrudes from the frame 210. Also, in the case where the enclosure 102 is mounted on the bridge 222, the enclosure 102 and the bridge 222 may also have any shape so that the enclosure 102 is embedded in the frame 210 without protruding from the frame 210.

FIG. 1 and FIG. 2 illustrate the structure in which the support portion 111 and the support portion 121 protrude from the front surface 182 of the enclosure 102; however, the structure is not limited to this. The support portion 111 and the support portion 121 may protrude from any surface of the enclosure 102. For example, the support portion 111 and the support portion 121 protrude from a bottom surface of the enclosure 102.

In FIG. 1 and FIG. 2, the example in which the hole 103 and the hole 104 are arranged in the front surface 182 of the enclosure 102 is given and described; however, the arrangement is not limited to this. The hole 103 and the hole 104 may also be arranged on an upper surface 184 of the enclosure 102. In this case, the hole 224 and the hole 226 may be arranged on an upper surface of the bridge 222.

In FIG. 1 and FIG. 2, the example is given and described, in which the pair of glasses 200 have the nose pad 242 and the nose pad 244 so that the pair of glasses 200 can be utilized even in the state in which the signal processing unit 100 is not mounted on the bridge 222; however, the pair of glasses 200 is not limited to this. The pair of glasses 200 may not have the nose pad 242 and the nose pad 244.

Figure 3:
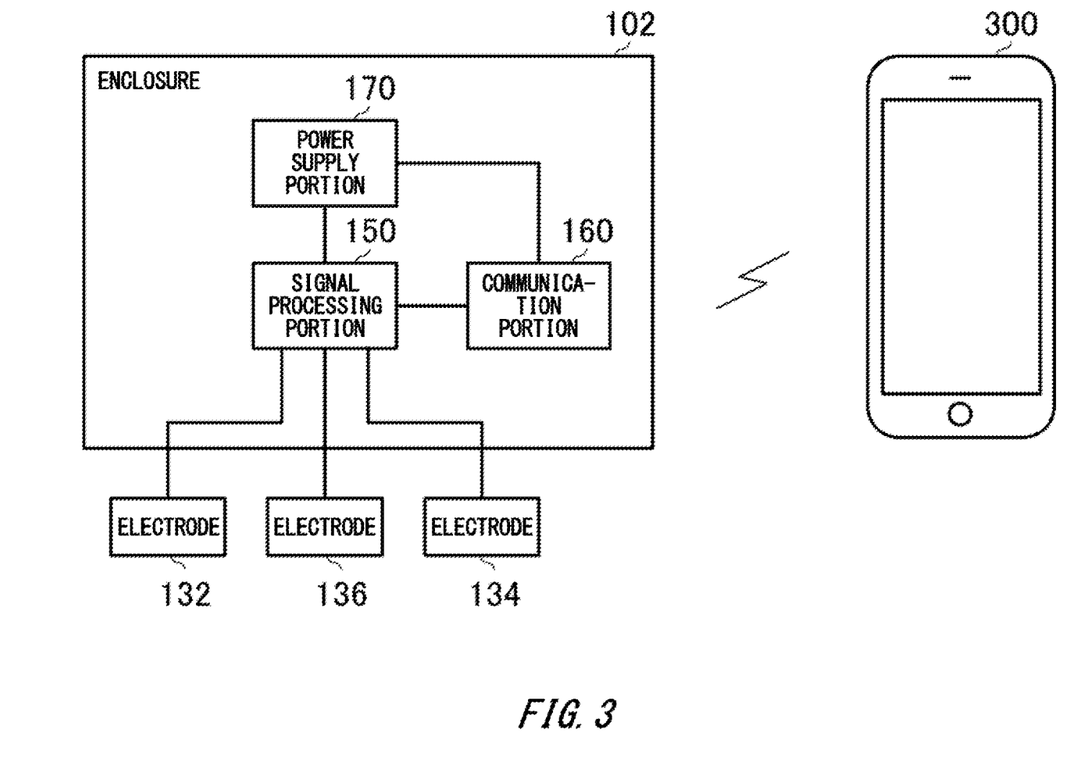
FIG. 3 schematically shows one example of a functional configuration of a signal processing unit 100.

FIG. 3 schematically shows one example of a functional configuration of the signal processing unit 100. The signal processing unit 100 includes a signal processing portion 150, a communication portion 160 and a power supply portion 170 that are arranged inside the enclosure 102.

The signal processing portion 150 processes the biomedical signal detected by the electrode 132, the electrode 134 and the electrode 136. The signal processing portion 150 may be a signal processing circuit. The signal processing portion 150 is achieved by a processor such as a Micro Processing Unit (MPU), for example.

The communication portion 160 transmits a processing result according to the signal processing portion 150 to an external device. FIG. 3 illustrates a smart phone 300 as one example of the external device. The external device may be any device as long as it can communicate with the communication portion 160. For example, the external device is a tablet terminal, a Personal Computer (PC), a car navigation system and the like.

The communication portion 160 may have a radio communication function. The communication portion 160 may conform to any wireless communication scheme. As the wireless communication scheme to which the communication portion 160 conforms, 3rd Generation (3G) wireless communication scheme, Long Term Evolution (LTE) wireless communication scheme, 4th Generation (4G) wireless communication scheme, 5th Generation (5G) and succeeding wireless communication schemes, Wireless Fidelity (Wi-Fi) (registered trademark), Bluetooth (registered trademark), ZigBee (registered trademark) and the like can be exemplified. The communication portion 160 may be a communication circuit. The communication portion 160 is achieved by a communication processor, for example.

The power supply portion 170 supplies electrical power to the signal processing portion 150 and the communication portion 160. The power supply portion 170 is achieved by any type of battery. The power supply portion 170 may be a so-called small-sized battery. The power supply portion 170 is a lithium-ion battery, for example.

The signal processing unit 100 is not electrically connected to the pair of glasses 200 even in the state in which the signal processing unit 100 is mounted on the pair of glasses 200. The signal processing unit 100 may be operable independently.

As an implementation example in which the pair of glasses is equipped with a function of processing the ocular potential of the wearer and transmitting the processing result to the external device, for example, there is an example in which the power supply portion 170 is arranged on one of the temples, a substrate having the signal processing portion 150 and the communication portion 160 is arranged on the other of the temples, and a wiring, which connects the power supply portion 170 and the substrate to electrodes installed on the nose pads and the like, is laid on the frame and/or embedded in the frame. According to this example, even if it is assumed that the power supply portion 170, the signal processing portion 150 and the communication portion 160 respectively had a certain size, by distributedly arranging the power supply portion 170, the signal processing portion 150 and the communication portion 160 on the pair of glasses, there is an advantage that all of them can be mounted on the pair of glasses; however, there are disadvantages that it becomes difficult to increase the types of the pair of glasses and at the same time, it becomes expensive in terms of mold and manufacturing costs and a mechanism also becomes complicated, and also, deterioration of the wiring caused by repeatedly folding the temples easily becomes an issue, and reliability as an electrical product becomes low easily.

On the other hand, the signal processing unit 100 according to the present embodiment can be independently operated because the electrical power is supplied to the signal processing portion 150 and the communication portion 160 by the power supply portion 170 installed inside the enclosure 102, the biomedical signal detected by the electrode 132, the electrode 134 and the electrode 136 is processed by the signal processing portion 150 installed inside the enclosure 102, and the processing result is transmitted to the external device by the communication portion 160 installed inside the enclosure 102. Also, because the signal processing unit 100 is attachable to and detachable from the pair of glasses 200, the signal processing unit 100 can be easily replaced to another pair of glasses 200.

In this way, according to the signal processing unit 100 according to the present embodiment, both of that the reliability as the pair of glasses 200 is maintained by dispensing with the wiring to the frame, and that a function as fashion is ensured by making the pair of glasses 200 be able to be freely selected by allowing the signal processing unit 100 to be exchangeable between a plurality of the pairs of glasses 200 can be achieved.

In the above described embodiment, the example in which the signal processing unit 100 has three electrodes (the electrode 132, the electrode 134 and the electrode 136) is given and described; however, the signal processing unit 100 is not limited to this and may also have two electrodes (the electrode 132 and the electrode 134).

Figure 4:
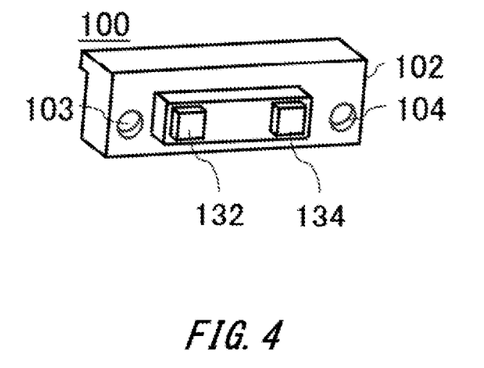
FIG. 4 schematically shows another example of the signal processing unit 100.

FIG. 4 schematically shows another example of the signal processing unit 100. Here, points different from the signal processing unit 100 shown in FIG. 1 to FIG. 3 are mainly described. In the example shown in FIG. 4, the signal processing unit 100 has the electrode 132 and the electrode 134 positioned to abut on the glabella of the wearer. The electrode 132 and the electrode 134 detect the biomedical signal of the wearer. The electrode 132 and the electrode 134 detect the ocular potential of the wearer, for example.

Figure 5:
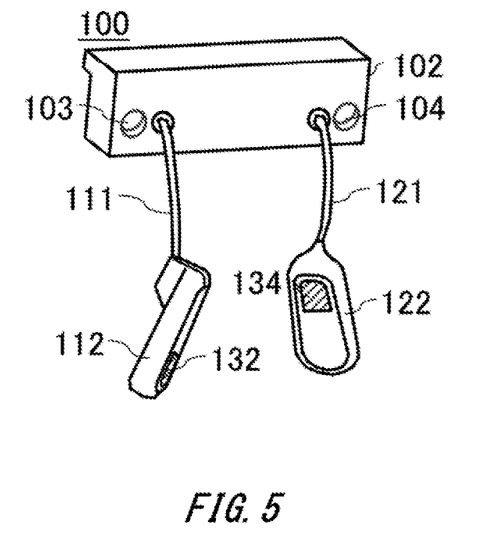
FIG. 5 schematically shows another example of the signal processing unit 100.

FIG. 5 schematically shows another example of the signal processing unit 100. Here, points different from the signal processing unit 100 shown in FIG. 1 to FIG. 3 are mainly described. In the example shown in FIG. 5, the signal processing unit 100 does not have the electrode 136 positioned to abut on the glabella of the wearer, and has the electrode 132 installed on a lower side than a center of the abutting portion 112 and the electrode 134 installed on an upper side than a center of the abutting portion 122. The electrode 132 and the electrode 134 detect the biomedical signal of the wearer. The electrode 132 and the electrode 134 detect the ocular potential of the wearer, for example.

In FIG. 5, the example in which the electrode 132 is installed on the lower side than the center of the abutting portion 112 and the electrode 134 is installed on the upper side than the center of the abutting portion 122 is given and described; however, the electrode 132 may also be installed on the upper side than the center of the abutting portion 112 and the electrode 134 may also be installed on the lower side than the center of the abutting portion 122. By shifting the upper/lower positions of the electrode 132 and the electrode 134, the electrode 136 can be dispensed with when detecting a visual line of the wearer, for example.

Figure 6:
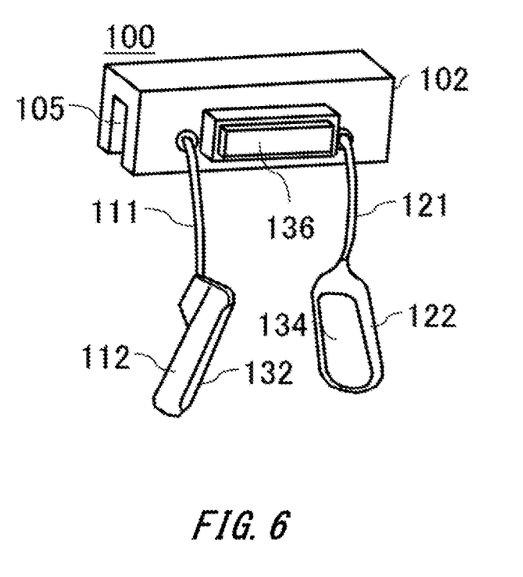
FIG. 6 schematically shows another example of the signal processing unit 100.

FIG. 6 schematically shows another example of the signal processing unit 100. Here, points different from the signal processing unit 100 shown in FIG. 1 to FIG. 3 are mainly described. In the example shown in FIG. 6, the signal processing unit 100 does not include the hole 103 and the hole 104, and includes the sandwiching portion 105. The sandwiching portion 105 may be one example of the mounting portion that attachably and detachably mounts the enclosure 102 on the bridge 222.

The sandwiching portion 105 sandwiches the frame 210 of the pair of glasses 200. The sandwiching portion 105 sandwiches a bridge of the frame 210, for example. In this case, the bridge of the frame 210 may be in a shape different from that of the bridge 222 shown in FIG. 1. The bridge of the frame 210 may have a shape so as to be sandwiched by the sandwiching portion 105.

The sandwiching portion 105 sandwiches the bridge of the frame 210 by having elasticity, for example. Also, the sandwiching portion 105 may also sandwich the bridge by that one of the sandwiching portion 105 and the bridge has a projecting portion, the other thereof has a recessed portion and the projecting portion is fitted into the recessed portion.

In the above described embodiment, the ocular potential is mainly given and described as the biomedical signal of a detection target; however, the biomedical signal is not limited to this. The biomedical signal of the detection target may also be a brain wave and the like. If the biomedical signal of the detection target is the brain wave, the configuration shown in FIG. 4 may be adopted, for example. Also, a configuration in which the abutting portion 112 and the abutting portion 122 protrude upward, not downward, and the electrode 132 and the electrode 134 are positioned to abut on a forehead of the wearer may also be adopted.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to", "before" or the like and as long as the output from a previous process is not used in a later process. Even if the process flow is described using phrases such as "first" or "next" in the claims, embodiments, or diagrams, it does not necessarily mean that the process must be performed in this order.

EXPLANATION OF REFERENCES

10 . . . eyewear set; 100 . . . signal processing unit; 102 . . . enclosure; 103 . . . hole; 104 . . . hole; 105 . . .

sandwiching portion; 111 . . . support portion; 112 . . . abutting portion; 121 . . . support portion; 122 . . . abutting portion; 132 . . . electrode; 134 . . . electrode; 136 . . . electrode; 150 . . . signal processing portion; 160 . . . communication portion; 170 . . . power supply portion; 182 . . . front surface; 184 . . . upper surface; 200 . . . glasses; 202 . . . lens; 210 . . . frame; 220 . . . front portion; 221 . . . rim; 222 . . . bridge; 224 . . . hole; 226 . . . hole; 242 . . . nose pad; 244 . . . nose pad; 250 . . . temple; 260 . . . temple; 270 . . . screw; 300 . . . smart phone

What is claimed is:

1. An eyewear set, comprising:
   an eyewear; and
   a signal processing unit that is attachable to and detachable from a bridge of the eyewear, wherein
   the signal processing unit includes:
   an enclosure;
   a first electrode and a second electrode that are mounted to the enclosure and operable to detect a biomedical signal of a wearer who is wearing the eyewear;
   a signal processing portion that is arranged inside the enclosure and processes the biomedical signal;
   a transmitting portion that is arranged inside the enclosure and transmits a processing result according to the signal processing portion to an external device;
   a power supply portion that is arranged inside the enclosure and supplies electrical power to the signal processing portion and the transmitting portion; and
   a mounting portion coupled to the enclosure, the mounting portion detachably attaching to the bridge to mount the signal processing unit to the eyewear; and wherein the eyewear and the signal processing unit are not electrically connected to each other while the signal processing unit is mounted to the eyewear.

2. The eyewear set according to claim 1, wherein
   the signal processing unit includes a pair of abutting portions configured to abut on a nose of the wearer, and
   the first electrode and the second electrode are installed on a surface of each of the pair of abutting portions and operable to detect an ocular potential of the wearer.

3. The eyewear set according to claim 2, wherein
   the signal processing unit includes a third electrode configured to abut on a glabella of the wearer.

4. The eyewear set according to claim 2, wherein
   the first electrode is installed on a lower side than a center of one of the pair of abutting portions, and the second electrode is provided on an upper side than a center of the other of the pair of abutting portions.

5. The eyewear set according to claim 2, wherein
   the signal processing unit includes a pair of support portions that support the pair of abutting portions, and
   if the signal processing unit is mounted on the eyewear, the pair of abutting portions function as nose pads.

6. The eyewear set according to claim 1, wherein the first electrode and the second electrode are configured to abut on a glabella of the wearer and operable to detect an ocular potential of the wearer.

7. The eyewear set according to claim 1, wherein the mounting portion includes a hole that communicates with a hole provided in the bridge.

8. The eyewear set according to claim 7, wherein the bridge has a structure that allows the signal processing unit to be fitted thereinto.

9. The eyewear set according to claim 1, wherein the bridge has a structure that allows the signal processing unit to be fitted thereinto.

10. The eyewear set according to claim 1, wherein the mounting portion mounts the enclosure on the bridge by sandwiching a frame of the eyewear.

11. A signal processing unit, comprising:
    an enclosure;
    a first electrode and a second electrode that are mounted to the enclosure and operable to detect a biomedical signal;
    a signal processing portion that is arranged inside the enclosure and processes the biomedical signal;
    a transmitting portion that is arranged inside the enclosure and transmits a processing result according to the signal processing portion to an external device;
    a power supply portion that is arranged inside the enclosure and supplies electrical power to the signal processing portion and the transmitting portion; and
    a mounting portion coupled to the enclosure, the mounting portion is configured to detachably mount to a bridge of an eyewear so that the signal processing unit and the eyewear are not electrically connected to each other when the signal processing unit is mounted to the eyewear.

* * * * *